(12) United States Patent
Ollendorf et al.

(10) Patent No.: US 7,219,995 B2
(45) Date of Patent: May 22, 2007

(54) APPARATUS FOR DETERMINING THE DISTANCE BETWEEN PUPILS

(76) Inventors: Hans-Joachim Ollendorf, Zur Springe 5, D-39517 Brunkau (DE); Peter Johann Haas, Gartenstrasse 4, D-39179 Barleben (DE)

( * ) Notice: Subject to any disclaimer, the term of this patent is extended or adjusted under 35 U.S.C. 154(b) by 463 days.

(21) Appl. No.: 10/925,434

(22) Filed: Aug. 25, 2004

(65) Prior Publication Data
US 2006/0061730 A1    Mar. 23, 2006

(51) Int. Cl.
*A61B 3/10* (2006.01)
*A61B 3/14* (2006.01)

(52) U.S. Cl. .................. 351/204; 351/206; 351/208

(58) Field of Classification Search ............... 351/204, 351/206, 208
See application file for complete search history.

(56) References Cited

U.S. PATENT DOCUMENTS 6,132,045 A * 10/2000 Gauvreau ................. 351/204
6,659,609 B2 * 12/2003 Mothes ..................... 351/204
6,692,127 B2 * 2/2004 Abitbol et al. ............. 351/227

FOREIGN PATENT DOCUMENTS

| DE | 43 23 384 C2 | 3/1994 |
| DE | 10005 801 A1 | 9/2000 |
| DE | 100 20 005 A | 11/2001 |

* cited by examiner

*Primary Examiner*—Jordan M. Schwartz
(74) *Attorney, Agent, or Firm*—Collard & Roe, P.C.

(57) ABSTRACT

An apparatus for determining the distance between the pupils to yield values representative of lenses properly aligned with the patient's pupils when mounted in the sockets of a spectacle frame. The apparatus consists of a calibration device having spaced fixed marking for placement in the plane of lenses, a camera with a zooming arrangement for taking an image of the subject, and a computer for generating parametric values relevant to the lenses to be ground as a function of the distance between the camera and the subject, the position of the zooming device at the time the image is taken, and the size of the image on the focal plane of the camera.

3 Claims, 2 Drawing Sheets

APPARATUS FOR DETERMINING THE DISTANCE BETWEEN PUPILS

BACKGROUND OF THE INVENTION

1. Field of the Invention

Figure 1:
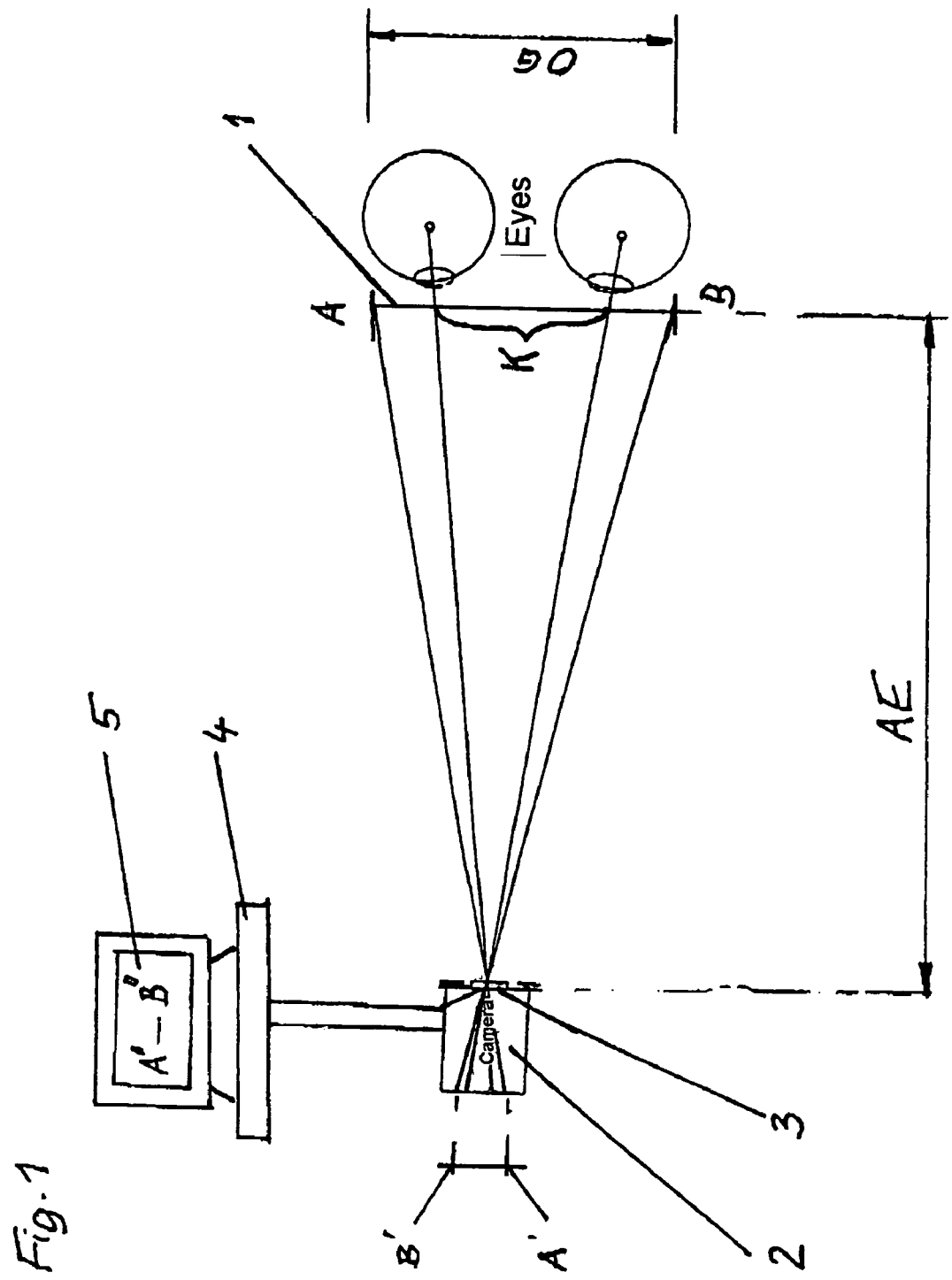

The invention relates to an apparatus as a component of a video centering system for determining the distance between pupils for precisely defining parameters relevant to the grinding of lenses to be mounted in the sockets of spectacles or eyeglasses.

2. The Prior Art

It is generally known that video systems are utilized for determining parameters relevant to grinding lenses of spectacles which are based upon producing a video photograph of a patient who is wearing the adjusted or fitted frame of his spectacles.

Thus, German patent specification DE 43 23 384 C2 describes a device for measuring the parameters requisite for conforming optical lenses to the frame of spectacles, particularly the distance between the pupils and the height of a person's pupils relative to the spectacle frame. The device is provided with a camera for taking a photograph of the head of the person wearing the spectacle frame and for adjustment with respect to the head. Furthermore, the device is provided with an electronic imaging unit for defining the parameters from the photograph of the head at a predetermined measured distance between the head and the camera. Within the camera, there is provided a coincidence range finder with an optical system behind the objective of the camera for separating the photograph into four adjacent images or partial images such that the correct measuring distance is obtained if the images or partial images join into a single image.

This device in essence consists of a camera to be aimed by its operator against a customer or patient with a follow-up optical system for determining the predetermined measured distance on the basis of a coincident distance measurement. Such an arrangement suffers from two disadvantages, however: It involves significant technical complexity to be made, and its manner of operation is such that measurement errors cannot be excluded.

German patent specification DE 100 20 005 A1 discloses an apparatus for, and a method of, defining the centering data for mounting lenses into spectacle frames. It utilizes a camera and a centering rider with a light source which compels a patient to look into a previously determined direction. Measurement data are read from a previously established centering foil, and the preferred light source is a laser pointer.

Another arrangement by which measuring the distance between the pupils of a human eye may be carried out digitally, is disclosed by German patent specification DE 100 05 801 A1. It proposes an examination frame for measuring the distance between the pupils of the patient's eyes. The examination frame consists of a lens support, a device for moving the lens support along the frame in the direction of the patient's nose or temple. In addition, the examination frame is provided with a source of electrical current and metal strips through which the current is flowing. By rotating the lens supports, the level of current flowing through the metal conductor is measured, and the distance between the pupils of the eyes of a given patient may be deduced from the measured current.

Such an arrangement may be said to suffer from the drawback that for the necessary corrective calculations, in particular the convergence or inward rotation of the eyes at a short viewing distance, it relies upon a shooting distance between the patient and the recording camera stored in the given systems data. In the event, the corrective calculations can be correct only to the extent that the stored values of shooting distances are adhered to during the exposures.

OBJECTS OF THE INVENTION

It is thus an object of the invention to provide an apparatus which serves as a component of a video centering system for determining the distance between the pupils for the exact or precise definition of parameters relevant to the grinding or fitting of lenses into spectacle frames and which substantially avoids the disadvantages of the prior art arrangements.

BRIEF SUMMARY OF THE INVENTION

In the accomplishment of these and other objects, the invention provides for an apparatus of the kind referred to for determining the distance between the pupils for exactly defining parameters relevant to the proper alignment of optical lenses to be mounted in the sockets of a spectacle frame, the apparatus being an integral component of a video centering system provided with a camera, a zooming device, a computer including monitor, and a calibrating device, in which the size of a subject is characterized by indicia on the calibration device disposed in the plane of the lens to be mounted in the socket to be measured and wherein the indicia recorded by the camera are transmitted to the computer for determining the actual value of the shooting distance which forms the basis of a value representative of the distance between the pupils.

Other objects will in part be obvious and will in part appear hereinafter.

The invention is based on the general recognition that, as a precondition, video systems useful for precisely determining all the parameters relevant to grinding lenses into spectacle frames such that they match the wearer's pupils function by a video photograph being taken of a patient with a frame of spectacles adjusted for a proper fit. The photograph is then measured on a monitor by software such that the position of the centers of the pupils of the eyes relative to the inner edges of the spectacle sockets are utilized as the grinding position of the lenses in the sockets of the spectacles to be made. The requisite corrective calculations and, more particularly, the convergence, are based upon values of the shooting distance between the patient and the recording camera stored in the given system data.

In accordance with the invention, the apparatus for determining the distance between the pupils is a component of a video centering system for defining the parameters relevant to grinding or fitting lenses into spectacle sockets. In a particularly advantageous embodiment of the invention, the shooting distance between a calibration device and a camera is determined as the value upon which the corrective calculations are based to derive the actual values of the distance between the pupils of a given patient.

A calibration device is mounted in the spectacle sockets such that it coincides with the plane of the lens. The calibration device is provided with two indicia at a fixed, defined and known spacing from each other. The calibration device is a component of the video centering system which is also equipped with a camera and a suitable zooming device as well as with a computer and a monitor or video screen.

The image size of the patient, i.e. the size of the subject or distance between the eyes of the patient is set on the monitor of the system by the operator of the video centering system by continuous or stepless adjustment of the focal length of the camera lens or zooming device, to a value relevant to the centering function.

At the time of the exposure, in addition to the image information (pixel), the actual value of the focal length (zoom factor) of the camera lens is also transmitted to the computer.

Thus, in accordance with the invention, there exists a fixed image scale relationship between the imaging size of the subject on the image plane of the camera and the imaging size on the monitor of the computer. Hence, there also exists a relationship between the size of the subject and the size of its image on the monitor, which depends upon the values of focal length of the camera lens and the distance of the subject from the camera.

In accordance with the invention, the size of the image of the subject on the monitor of the computer is determined by evaluation software either by the operator of the video centering system or automatically. The focal length of the camera lens at the time of the exposure as well as the original size of the subject are known. Thus, the distance between the subject and the camera, i.e. the shooting distance, is determined by previously determined parametric or field functions specific to the camera. The shooting distance forms the basis of the corrective calculations of the convergence. It is thus the basis for determining the actually required or correct value of the distance between the pupils of the eyes of the patient.

DESCRIPTION OF THE SEVERAL DRAWINGS

Figure 2:
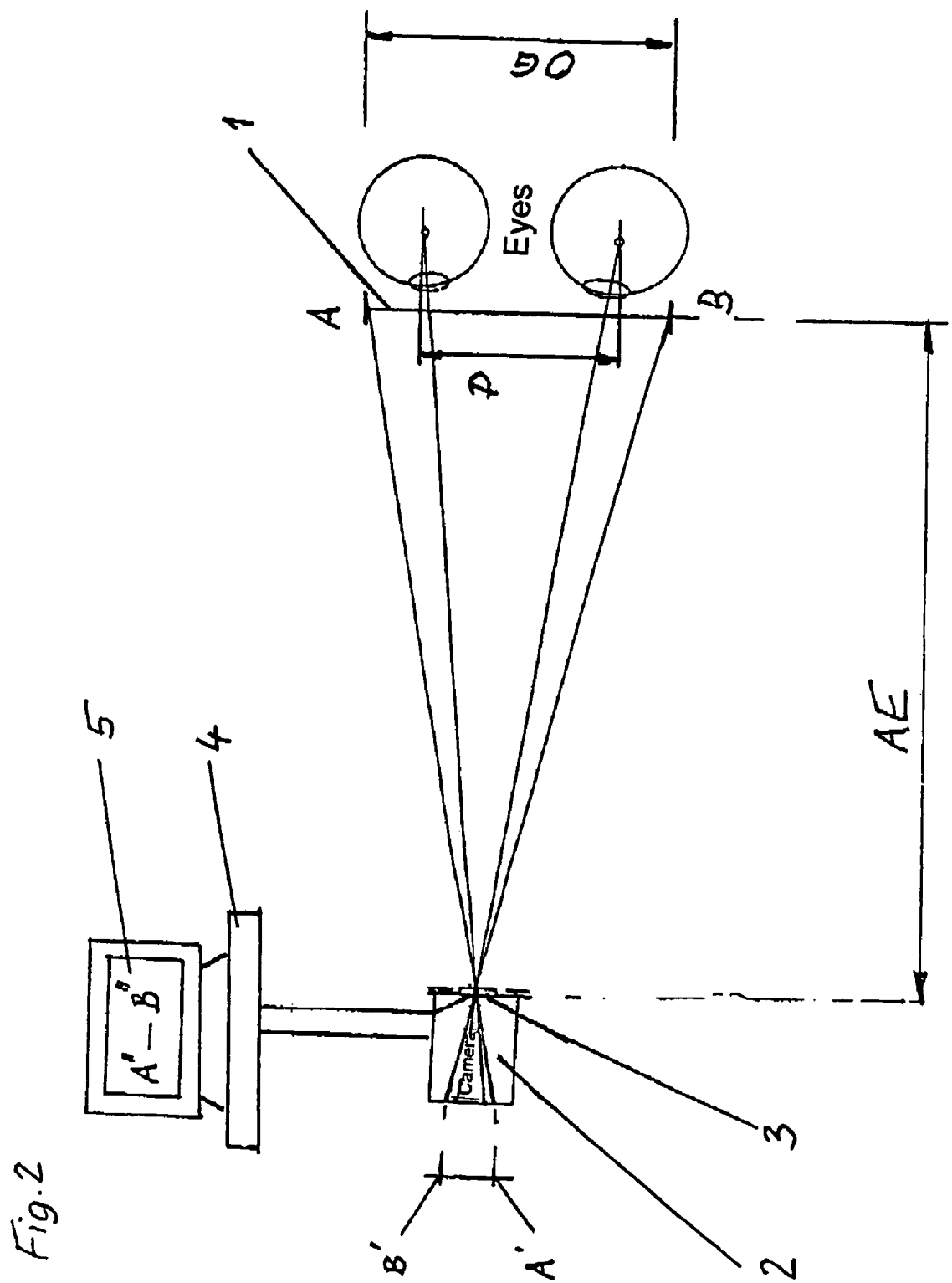

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended drawings, in which:

FIG. 1 schematically depicts the complete apparatus;

FIG. 2 schematically depicts the complete apparatus with the determined actual values of the distance between pupils following a measurement.

DETAILED DESCRIPTION OF THE PREFERRED EMBODIMENTS

The complete video centering system for precisely defining the parameters relevant to grinding or fitting lenses into spectacle sockets of which the apparatus for determining the distance between pupils forms an integral component, may be seen in FIG. 1.

The video centering system consists of a calibration unit 1, a camera 2 including a zooming device 3 as well as of a computer 4 and a monitor 5 associated therewith.

The meaning of the reference characters used in FIGS. 1 and 2 is as follows:

A; B indicia;

K convergence, i.e. the converged orientation of the eyes;

AE shooting distance;

OG size of the subject;

P the correct position of the eyes/distance between pupils.

A calibration device 1 is placed into the socket of the spectacles to be measured of the patient to coincide with the plane of the lens of the spectacle. The calibration device 1 is provided with two indicia A; B which are spaced from each other by a fixed, defined, and known distance and which define the size OG of the subject.

A mirror image labeled A' and B' in FIG. 1 is taken with the camera 2 and the zooming device 3 thereof. The camera 2 is connected to the computer 4 and its monitor 5 so that the indicia A' and B' may bet transmitted to it and rendered visible on the monitor 5. On the screen of the monitor 5, these parameters are presented by indicia A" and B".

In addition to, and simultaneously with, the transmission of indicia A' and B' from the camera 2 to the monitor 5, the zoom position of the lens of the camera 2 is also transmitted to the computer 4 and the monitor 5.

The image of the subject size OG of the patient is adjusted on the monitor 5 to a value relevant to the centering function, by continuous or stepless adjustment of the focal length of the zooming device 3, by the operator of the video centering system. In addition to the image data, the actual value of the focal length of the zooming device 3 is also transmitted to the computer 4 at the time of the exposure. A fixed image scale relationship exists between the size OG of the image, shown here as indicia A' and B', on the focal plane of the camera 2 and the image size of the subject on the monitor 5 as shown by indicia A" and B".

Thus, there also exists a relationship depending upon the values of the zooming device 3 of the camera 2 relative to the distance of the subject from the camera 2, between the size OG of the subject shown by indicia A and B and the image size of the subject on the monitor 5 shown by indicia A" and B". As shown in FIG. 1, the size OG of the subject is displayed on the calibration device 1 by indicia A and B. The converged orientation of the eyes/pupils at the time of taking the exposure is shown by reference character K. The distance between the calibration device 1 and the camera 2 represents the shooting distance AE.

The image size of the object on the monitor 5 is determined with suitable software either by the operator of the system or automatically, as shown by indicia A" and B" in FIGS. 1 and 2. The zooming position of the camera 2 at the time of the exposure is known as is the original size OG of the subject depicted by indicia A and B on the calibration device 1. The precise shooting distance AE is defined by taking these known values into account. The precise shooting distance AE then forms the basis upon which the correct positional values of the pupils of the eyes of a patient, shown in FIG. 2 by reference character P, is determined. In this manner the parameters are established which are relevant to the grinding of lenses such that when mounted in the sockets of a spectacle they are properly aligned with the pupils of a patient.

What is claimed is:

1. An apparatus for determining the distance between the pupils for defining precisely the parameters relevant to grinding spectacle lenses for the alignment of optical lenses in a spectacle frame, as an integral component of a video centering system provided with a camera (2), a zooming device (3), a computer (4) with a monitor (5) and a calibration device (1) in which the size (OG) of the subject is presented by indicia (A; B) on the calibration device (1) disposed in the plane of the spectacle lens of the spectacle socket to be measured, the indicia (A; B) being detected by the camera (2) and transmitted to the computer (4) for determining the actual value of the shooting distance (AE)

which forms the basis for the value of the position (P) of the distance between the pupils.

2. The apparatus of claim 1, characterized by a fixed image scale relationship between the image size of the subject in the indicia (A; B) on the focal plane of the camera (2) in the indicia (A'; B') and the size of the image on the monitor (5) of the computer (4) in the indicia (A"; B").

3. The apparatus of claims 1, characterized by a relationship dependent upon the values of the zooming device (3) of the camera (2) and the distance of the subject from the camera (2) existing between the size of the subject (OG) and its image size (A"; B") on the monitor.

* * * * *